(12) United States Patent
Helenek et al.

(10) Patent No.: US 7,754,702 B2
(45) Date of Patent: Jul. 13, 2010

(54) METHODS AND COMPOSITIONS FOR ADMINISTRATION OF IRON

(75) Inventors: Mary Jane Helenek, Brookville, NY (US); Marc L. Tokars, Douglassville, PA (US); Richard P. Lawrence, Calverton, NY (US)

(73) Assignee: Luitpold Pharmaceuticals, Inc., Shirley, NY (US)

( * ) Notice: Subject to any disclaimer, the term of this patent is extended or adjusted under 35 U.S.C. 154(b) by 403 days.

(21) Appl. No.: 11/620,986

(22) Filed: Jan. 8, 2007

(65) Prior Publication Data

US 2007/0161600 A1   Jul. 12, 2007

Related U.S. Application Data

(60) Provisional application No. 60/757,119, filed on Jan. 6, 2006.

(51) Int. Cl.
*A61K 31/715* (2006.01)
*A61K 31/716* (2006.01)

(52) U.S. Cl. ............... 514/54; 556/146; 536/123.1; 536/123.12; 536/123.13

(58) Field of Classification Search ............ 514/53, 514/54; 556/146
See application file for complete search history.

(56) References Cited

U.S. PATENT DOCUMENTS

| | | | |
|---|---|---|---|
| 5,624,668 A * | 4/1997 | Lawrence et al. | 424/78.17 |
| 6,599,498 B1 | 7/2003 | Groman et al. | |
| 6,960,571 B2 | 11/2005 | Helenek et al. | |
| 2004/0180849 A1 * | 9/2004 | Helenek et al. | 514/53 |

FOREIGN PATENT DOCUMENTS

| WO | 9711711 | 4/1997 |
|---|---|---|
| WO | 2004037865 | 5/2004 |
| WO | 2007023154 | 3/2007 |

OTHER PUBLICATIONS

Sofic et al. J. Neural Transm, 1988, 74, p. 199-205.*
Sipe et al. Brain Iron Metabolism and Neurodegenerative Disorders, 2002, 24(2-3), p. 188-196.*
Cisar et al. Journal of Experimental Medicine, 1975, 142, p. 435-459.*
Macdougall. Nephrol. Dial. Transplant, 2000, 15, p. 1743-1745.*
Andersson, NSE. British Medical Journal, 1961, p. 275-279.*
Fielding, J. British Medical Journal, 1961, p. 279-283.*
Newnham et al. Internal Medicine Journal, 2006, 36(10), p. 672-674.*
Haines et al. Internal Medicine Journal, 2009, 39, p. 252-255.*
Nissenson et al. Kidney International, 2003, 64(Supplement 87), p. S64-S71.*
Bailie GR, et al., Hypersensitivity reactions and deaths associated with intravenous iron preparations, Nephrol. Dial. Transplant, 2005, pp. 1443-1449, vol. 20(7).
Beshara S, et al., Pharmacokinetics and red cell utilization of 52Fe/59Fe-labelled iron polymaltose in anaemic patients using positron emission tomography, Br. J. Haematol., 2003, pp. 853-859, vol. 120(5).
Fishbane S, Safety in iron management, Am. J. Kidney Dis., 2003, pp. 19-26, vol. 41(5 Suppl).
Geisser P, et al., Structure/histotoxicity relationship of parenteral iron preparations, Arzneimittelforschung, 1992, pp. 1439-1452, vol. 42(12).
Kudasheva DS, et al., Structure of carbohydrate-bound polynuclear iron oxyhydroxide nanoparticles in parenteral formulations, J. Inorg. Biochem., 2004, pp. 1757-1769, vol. 98(11).
Landry R, et al., Pharmacokinetic study of ferumoxytol: a new iron replacement therapy in normal subjects and hemodialysis patients, Am. J. Nephrol., 2005, pp. 400-410, vol. 25(4).
NKF-K/DOQI Clinical Practice Guidelines for Anemia of Chronic Kidney Disease: update 2000, Am. J. Kidney Dis., 2001, pp. S182-S238, vol. 37(1 Suppl 1).
Spinowitz BS, et al., The safety and efficacy of ferumoxytol therapy in anemic chronic kidney disease patients, Kidney Int., 2005, pp. 1801-1807, vol. 68(4).
Van Wyck DB, et al., Making sense: a scientific approach to intravenous iron therapy, J. Am. Soc. Nephrol., 2004, pp. S91-S92, vol. 15 Suppl 2.
Van Wyck DB, Labile iron: manifestations and clinical implications, J. Am. Soc. Nephrol., 2004, pp. S107-S111, vol. 15 Suppl 2.
European Search Report issued Oct. 21, 2009 in connection with related European Application No. 07716309.5.

* cited by examiner

*Primary Examiner*—Shaojia Anna Jiang
*Assistant Examiner*—Jonathan S Lau
(74) *Attorney, Agent, or Firm*—Sonnenschein Nath & Rosenthal LLP

(57) ABSTRACT

The present invention generally relates to treatment of iron-related conditions with iron carbohydrate complexes. One aspect of the invention is a method of treatment of iron-related conditions with a single unit dosage of at least about 0.6 grams of elemental iron via an iron carbohydrate complex. The method generally employs iron carbohydrate complexes with nearly neutral pH, physiological osmolarity, and stable and non-immunogenic carbohydrate components so as to rapidly administer high single unit doses of iron intravenously to patients in need thereof.

57 Claims, 2 Drawing Sheets

FIGURE 1
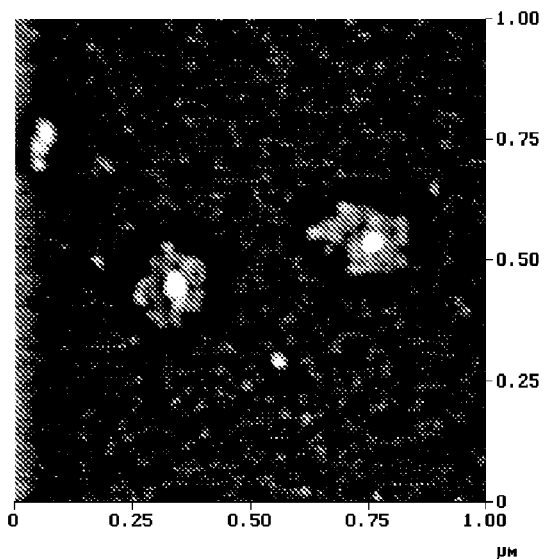
FIG. 1A
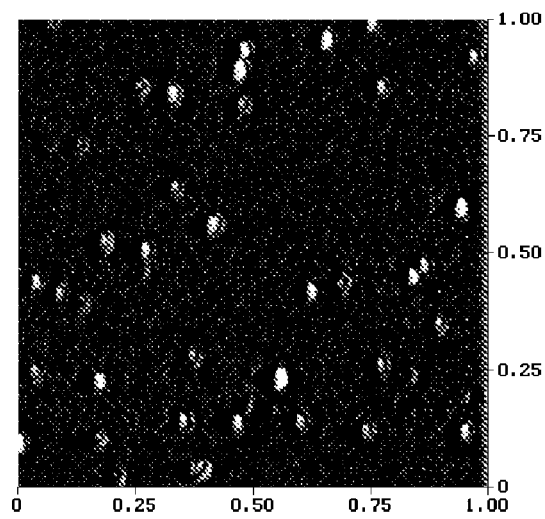
FIG. 1B
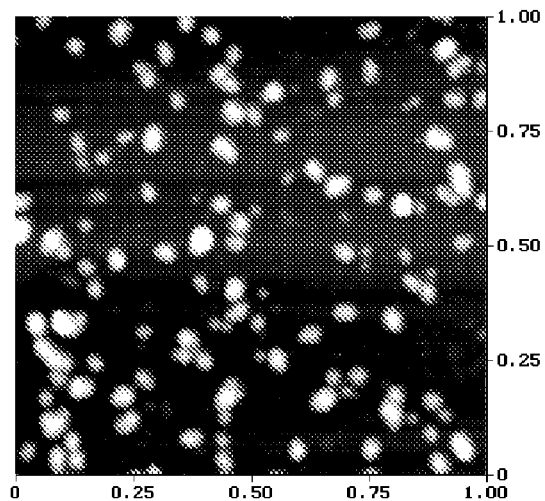
FIG. 1C

METHODS AND COMPOSITIONS FOR ADMINISTRATION OF IRON

CROSS-REFERENCE TO RELATED APPLICATIONS

This application claims priority from U.S. Provisional Application Ser. No. 60/757,119 filed on Jan. 6, 2006, which is incorporated herein by reference in its entirety.

FIELD OF THE INVENTION

The present invention generally relates to treatment of iron-related conditions with iron carbohydrate complexes.

BACKGROUND

Parenteral iron therapy is known to be effective in a variety of diseases and conditions including, but not limited to, severe iron deficiency, iron deficiency anemia, problems of intestinal iron absorption, intestinal iron intolerance, cases where regular intake of an oral iron preparation is not guaranteed, iron deficiency where there is no response to oral therapy (e.g., dialysis patients), and situations where iron stores are scarcely or not at all formed but would be important for further therapy (e.g., in combination with erythropoietin). Geisser et al., Arzneimittelforschung (1992) 42(12), 1439-1452. There exist various commercially available parenteral iron formulations. But many currently available parenteral iron drugs, while purportedly effective at repleting iron stores, have health risks and dosage limitations associated with their use.

Currently available parenteral iron formulations approved for use in the U.S. include iron dextran (e.g., InFed, Dexferrum), sodium ferric gluconate complex in sucrose (Ferrlecit), and iron sucrose (Venofer). Although serious and life-threatening reactions occur most frequently with iron dextran, they are also known to occur with other parenteral iron products. In addition, non-life threatening reactions such as arthralgia, back pain, hypotension, fever, myalgia, pruritus, vertigo, and vomiting also occur. These reactions, while not life-threatening, often preclude further dosing and therefore iron repletion.

Iron dextran, the first parenteral iron product available in the United States (US), has been associated with an incidence of anaphylactoid-type reactions (i.e., dyspnea, wheezing, chest pain, hypotension, urticaria, angioedema). See generally Fishbane, Am J Kidney Dis (2003) 41 (5Suppl), 18-26; Landry et al. (2005) Am J Nephrol 25, 400-410, 407. This high incidence of anaphylactoid reactions is believed to be caused by the formation of antibodies to the dextran moiety. Other parenteral iron products (e.g., iron sucrose and iron gluconate) do not contain the dextran moiety, and the incidence of anaphylaxis with these products is markedly lower. Fishbane, Am J Kidney Dis (2003) 41(5Suppl), 18-26; Geisser et al., Arzneimittelforschung (1992) 42(12), 1439-52. However, the physical characteristics of, for example, iron gluconate and iron sucrose lead to dosage and administration rate limitations. Negative characteristics include high pH, high osmolarity, low dosage limits (e.g., maximum 500 mg iron once per week, not exceeding 7 mg iron/kg body weight), and the long duration of administration (e.g., 100 mg iron over at least 5 minutes as an injection; 500 mg iron over at least 3.5 hours as a drip infusion). Furthermore, injectable high molecular mass substances produce more allergic reactions than the corresponding low molecular mass substances. Geisser et al. (1992) Arzneimittelforschung 42: 1439-1452.

Ferumoxytol is a newer parenteral iron formulation but limited information is available as to its efficacy and administration. See e.g., Landry et al. (2005) Am J Nephrol 25, 400-410, 408; and Spinowitz et al. (2005) Kidney Intl 68, 1801-1807; U.S. Pat. No. 6,599,498.

Various pharmacokinetic studies suggest that doses of iron complexes higher than 200 mg of iron are generally unsuitable and that the conventional therapy model prescribes repeated applications of lower doses over several days. See Geisser et al., (1992) Arzneimittelforschung 42: 1439-1452. For example, to achieve iron repletion under current therapy models, a total dose of 1 g typically requires 5 to 10 sessions over an extended period of time. These delivery modes incur significant expense for supplies such as tubing and infusate, costly nursing time, multiple administrations, and patient inconvenience.

SUMMARY OF THE INVENTION

Among the various aspects of the present invention is the provision of a method of treatment of iron-associated diseases, disorders, or conditions with iron formulations. Briefly, therefore, the present invention is directed to use of iron carbohydrate complexes that can be administered parenterally at relatively high single unit dosages, thereby providing a safe and efficient means for delivery of a total dose of iron in fewer sessions over the course of therapeutic treatment.

The present teachings include methods of treating a disease, disorder, or condition characterized by iron deficiency or dysfunctional iron metabolism through the administration of at least 0.6 grams of elemental iron via a single unit dosage of an iron carbohydrate complex to a subject that is in need of such therapy.

In various embodiments, the method treats anemia. In some embodiments, the anemia is an iron deficiency anemia, such as that associated with chronic blood loss; acute blood loss; pregnancy; childbirth; childhood development; psychomotor and cognitive development in children; breath holding spells; heavy uterine bleeding; menstruation; chronic recurrent hemoptysis; idiopathic pulmonary siderosis; chronic internal bleeding; gastrointestinal bleeding; parasitic infections; chronic kidney disease; dialysis; surgery or acute trauma; and chronic ingestion of alcohol, chronic ingestion of salicylates, chronic ingestion of steroids; chronic ingestion of non-steroidial anti-inflammatory agents, or chronic ingestion of erythropoiesis stimulating agents. In some aspects, the anemia is anemia of chronic disease, such as rheumatoid arthritis; cancer; Hodgkins leukemia; non-Hodgkins leukemia; cancer chemotherapy; inflammatory bowel disease; ulcerative colitis thyroiditis; hepatitis; systemic lupus erythematosus; polymyalgia rheumatica; scleroderma; mixed connective tissue disease; Sojgren's syndrome; congestive heart failure/cardiomyopathy; or idiopathic geriatric anemia. In some embodiments, the anemia is due to impaired iron absorption or poor nutrition, such as anemia associated with Crohn's Disease; gastric surgery; ingestion of drug products that inhibit iron absorption; and chronic use of calcium. In various embodiments, the method treats restless leg syndrome; blood donation; Parkinson's disease; hair loss; or attention deficit disorder.

In various embodiments, the single dosage unit of elemental iron is between at least about 0.6 grams and 2.5 grams. In some embodiments, the single dosage unit of elemental iron is at least about 0.7 grams; at least about 0.8 grams; at least about 0.9 grams; at least about 1.0 grams; at least about 1.1 grams; at least about 1.2 grams; at least about 1.3 grams; at least about 1.4 grams; at least about 1.5 grams; at least about 1.6 grams; at least about 1.7 grams; at least about 1.8 grams; at least about 1.9 grams; at least about 2.0 grams; at least about 2.1 grams; at least about 2.2 grams; at least about 2.3 grams; at least about 2.4 grams; or at least about 2.5 grams.

In various embodiments, the single dosage unit of elemental iron is administered in about 15 minutes or less. In some embodiments, the single dosage unit of elemental iron is administered in about 10 minutes or less, about 5 minutes or less, or about 2 minutes or less.

In various embodiments, the subject does not experience a significant adverse reaction to the single dosage unit administration.

In various embodiments, the iron carbohydrate complex has a pH between about 5.0 to about 7.0; physiological osmolarity; an iron core size no greater than about 9 nm; a mean diameter particle size no greater than about 35 nm; a blood half-life of between about 10 hours to about 20 hours; a substantially non-immunogenic carbohydrate component; and substantially no cross reactivity with anti-dextran antibodies.

In various embodiments, the iron carbohydrate complex contains about 24% to about 32% elemental iron; contains about 25% to about 50% carbohydrate; has a molecular weight of about 90,000 daltons to about 800,000 daltons, or some combination thereof.

In various embodiments, the iron carbohydrate complex is an iron monosaccharide complex, an iron disaccharide complex, or an iron polysaccharide complex. In some embodiments, the iron carbohydrate complex is iron carboxymaltose complex, iron mannitol complex, iron polyisomaltose complex, iron polymaltose complex, iron gluconate complex, iron sorbitol complex, or an iron hydrogenated dextran complex. In some embodiments, the iron carbohydrate complex is an iron polyglucose sorbitol carboxymethyl ether complex. In some preferred embodiments, the iron carboxymaltose complex contains about 24% to about 32% elemental iron, about 25% to about 50% carbohydrate, and is about 100,000 daltons to about 350,000 daltons. In some preferred embodiments, the iron carboxymaltose complex is obtained from an aqueous solution of iron (III) salt and an aqueous solution of the oxidation product of one or more maltodextrins using an aqueous hypochlorite solution at a pH value within the alkaline range, wherein, when one maltodextrin is applied, its dextrose equivalent lies between 5 and 20, and when a mixture of several maltodextrins is applied, the dextrose equivalent lies between 5 and 20 and the dextrose equivalent of each individual maltodextrin contained in the mixture lies between 2 and 20. In some preferred embodiments, the iron carboxymaltose complex has a chemical formula of $[FeO_x(OH)_y(H_2O)_z]_n[\{(C_6H_{10}O_5)_m(C_6H_{12}O_7)\}_l]_k$, where n is about 103, m is about 8, l is about 11, and k is about 4; contains about 28% elemental iron; and has a molecular weight of about 150,000 Da. In some preferred embodiments, the iron carboxymaltose complex is polynuclear iron (III)-hydroxide 4(R)-(poly-(1→4)-O-α-glucopyranosyl)-oxy-2(R),3(S),5(R),6-tetrahydroxy-hexanoate.

In various embodiments, the iron carbohydrate complex comprises an iron core with a mean iron core size of no greater than about 9 nm. In some embodiments, the mean iron core size is at least about 1 nm but no greater than about 9 nm; at least about 3 nm but no greater than about 7 nm; or at least about 4 nm but not greater than about 5 nm.

In various embodiments, the mean size of a particle of the iron carbohydrate complex is no greater than about 35 nm. In some embodiments, the particle mean size is no greater than about 30 nm. In some embodiments, the particle mean size is no greater than about 25 nm. In some embodiments, the particle mean size is no greater than about 20 nm; no greater than about 15 nm; no greater than about 10 nm; or at least about 6 nm but no greater than about 7 nm.

In various embodiments, the iron carbohydrate complex is administered parenterally, for example intravenously or intramuscularly. In some embodiments, the iron carbohydrate complex is intravenously infused. In certain embodiments, the single unit dose of iron carbohydrate complex is intravenously infused at a concentration of about 1000 mg elemental iron in about 200 ml to about 300 ml of diluent, for example, about 250 ml of diluent or about 215 ml of diluent. In some embodiments, the iron carbohydrate complex is intravenously injected as a bolus. In certain embodiments, the iron carbohydrate complex is intravenously injected as a bolus at a concentration of about 1000 mg elemental iron in about 200 ml to about 300 ml of diluent, for example, about 250 ml of diluent or about 215 ml of diluent. In some embodiments, the iron carbohydrate complex is intramuscularly infused at a concentration of about 1000 mg elemental iron in about 200 ml to about 300 ml of diluent, for example, about 250 ml of diluent or about 215 ml of diluent. In some embodiments, the iron carbohydrate complex is intramuscularly infused at a concentration of about 500 mg elemental iron in less than about 10 ml diluent.

In various embodiments, the method also includes a second administration of the iron carbohydrate complex upon recurrence of at least one symptom of the treated disease, disorder, or condition.

In various embodiments, the method also includes a second administration of the iron carbohydrate complex after 1 day to 12 months after the first administration.

In a preferred embodiment, the method of treating a disease, disorder, or condition characterized by iron deficiency or dysfunctional iron metabolism comprises intravenously administering to a subject in need thereof an iron carboxymaltose complex in a single dosage unit of at least about 1000 mg of elemental iron in about 200 ml to about 300 ml of diluent in about 5 minutes or less; wherein the iron carboxymaltose complex comprises an iron core with a mean iron core size of at least about 1 nm but no greater than about 9 nm; mean size of a particle of the iron carboxymaltose complex is no greater than about 35 nm; and the iron carboxymaltose complex is administered intravenously infused or intravenously injected at a concentration of about 1000 mg elemental iron in about 200 ml to about 300 ml of diluent. In some these embodiments, the iron carboxymaltose complex is polynuclear iron (III)-hydroxide 4(R)-(poly-(1→4)-O-α-glucopyranosyl)-oxy-2(R),3(S),5(R),6-tetrahydroxy-hexanoate. In some these embodiments, the iron carboxymaltose complex is obtained from an aqueous solution of iron (III) salt and an aqueous solution of the oxidation product of one or more maltodextrins using an aqueous hypochlorite solution at a pH value within the alkaline range, wherein, when one maltodextrin is applied, its dextrose equivalent lies between about 5 and about 20, and when a mixture of several maltodextrins is applied, the dextrose equivalent lies between about 5 and about 20 and the dextrose equivalent of each individual maltodextrin contained in the mixture lies between about 2 and about 20.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 1 is a series of electron micrographs that depict the particle size of three iron carbohydrate complexes. FIG. 1A is an electron micrograph depicting the particle size of Dexferrum (an iron dextran). FIG. 1B is an electron micrograph depicting the particle size of Venofer (an iron sucrose). FIG. 1C is an electron micrograph depicting the particle size of polynuclear iron (III)-hydroxide 4(R)-(poly-(1→4)-O-α-glucopyranosyl)-oxy-2(R),3(S),5(R),6-tetrahydroxy-hexanoate ("VIT-45", an iron carboxymaltose complex).

DETAILED DESCRIPTION OF THE INVENTION

Figure 2:
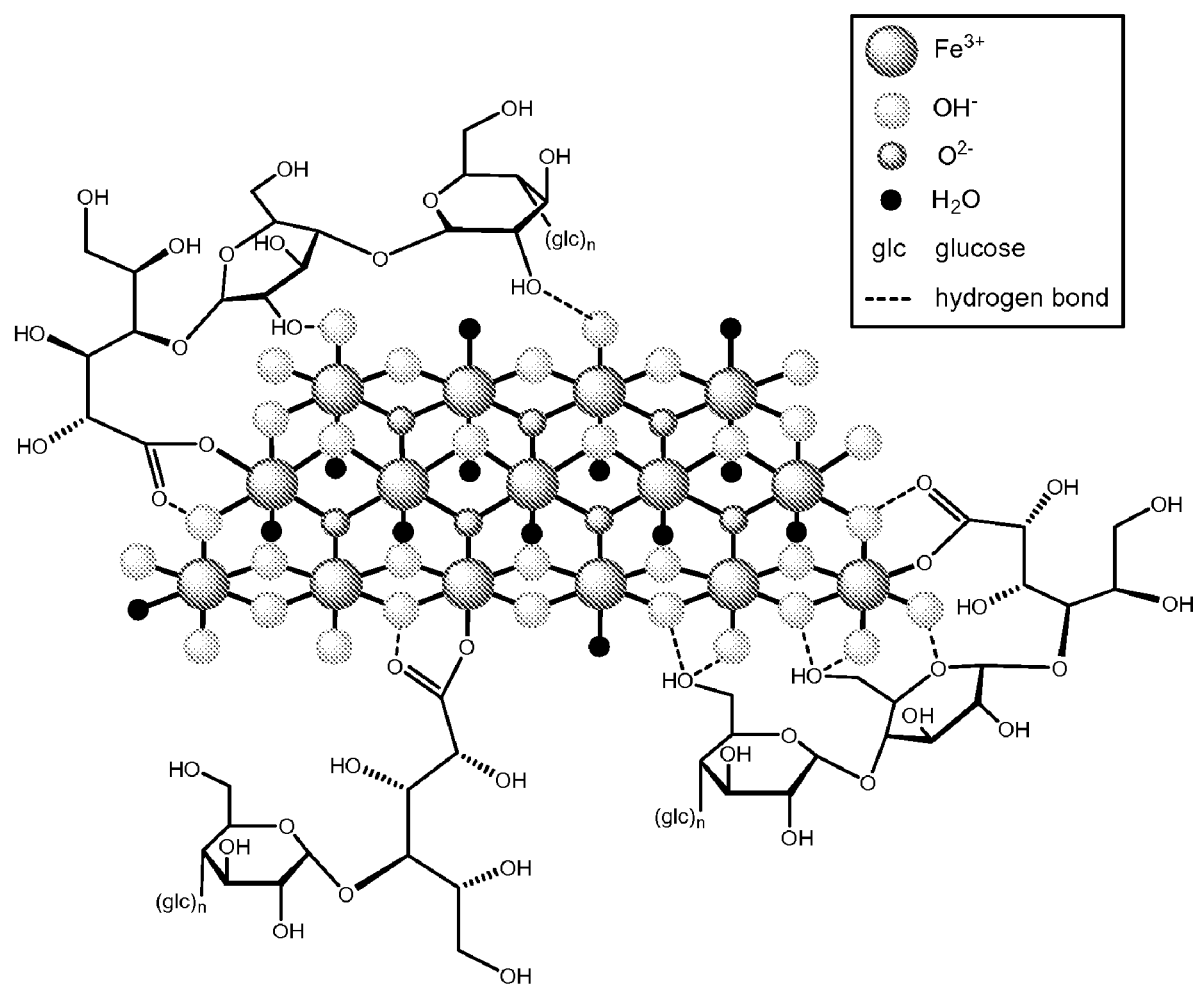
FIG. 2 is a schematic representation of an exemplary iron carboxymaltose complex.

The present invention makes use of iron carbohydrate complexes that can be administered parenterally at relatively high single unit dosages for the therapeutic treatment of a variety of iron-associated diseases, disorders, or conditions. Generally, states indicative of a need for therapy with high single unit dosages of iron carbohydrate complexes include, but are not limited to iron deficiency anemia, anemia of chronic disease, and states characterized by dysfunctional iron metabolism. Efficacious treatment of these, and other, diseases and conditions with parenteral iron formulations (supplied at lower single unit dosages than those described herein) is generally known in the art. See e.g., Van Wyck et al. (2004) J Am Soc Nephrol 15, S91-S92. The present invention is directed to use of iron carbohydrate complexes that can be administered parenterally at relatively high single unit dosages, thereby providing a safe and efficient means for delivery of a total dose of iron in fewer sessions over the course of therapeutic treatment.

Iron deficiency anemia is associated with, for example, chronic blood loss; acute blood loss; pregnancy; childbirth; childhood development; psychomotor and cognitive development in children; breath holding spells; heavy uterine bleeding; menstruation; chronic recurrent hemoptysis; idiopathic pulmonary siderosis; chronic internal bleeding; gastrointestinal bleeding; parasitic infections; chronic kidney disease; dialysis; surgery or acute trauma; and chronic ingestion of alcohol, chronic ingestion of salicylates, chronic ingestion of steroids; chronic ingestion of non-steroidial anti-inflammatory agents, or chronic ingestion of erythropoiesis stimulating agents.

Anemia of chronic disease is associated with, for example, rheumatoid arthritis; cancer; Hodgkins leukemia; non-Hodgkins leukemia; cancer chemotherapy; inflammatory bowel disease; ulcerative colitis thyroiditis; hepatitis; systemic lupus erythematosus; polymyalgia rheumatica; scleroderma; mixed connective tissue disease; Sojgren's syndrome; congestive heart failure/cardiomyopathy; and idiopathic geriatric anemia.

Anemia is also associated with, for example, Crohn's Disease; gastric surgery; ingestion of drug products that inhibit iron absorption; and chronic use of calcium.

States characterized by dysfunctional iron metabolism and treatable with the single unit dosages of iron carbohydrate complexes described herein include, but are not limited to, restless leg syndrome; blood donation; Parkinson's disease; hair loss; and attention deficit disorder.

Again, each of the above listed states, diseases, disorders, and conditions, as well as others, can benefit from the treatment methodologies described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms.

The benefit to a subject to be treated is either statistically significant or at least perceptible to the patient or to the physician. Measures of efficacy of iron replacement therapy are generally based on measurement of iron-related parameters in blood. The aim of treatment is usually to return both Hb and iron stores to normal levels. Thus, efficacy of iron replacement therapy can be interpreted in terms of the ability to normalise Hb levels and iron stores. The effectiveness of treatment with one or more single unit doses of iron carbohydrate complex, as described herein, can be demonstrated, for example, by improvements in ferritin and transferrin saturation, and in raising hemoglobin levels in anemic patients. Iron stores can be assessed by interpreting serum ferritin levels. TfS is frequently used, in addition, to diagnose absolute or functional iron deficiencies. In patients with iron deficiency, serum transferrin is elevated and will decrease following successful iron treatment.

Administration

Methods of treatment of various diseases, disorders, or conditions with iron complex compositions comprise the administration of the complex in single unit dosages of at least 0.6 grams of elemental iron to about at least 2.5 grams of elemental iron. Administration of single unit dosages can be, for example, over pre-determined time intervals or in response to the appearance and/or reappearance of symptoms. For example, the iron carbohydrate complex can be re-administered upon recurrence of at least one symptom of the disease or disorder. As another example, the iron carbohydrate complex can be re-administered at some time period after the initial administration (e.g., after 4 days to 12 months).

Any route of delivery of the single unit dose of iron carbohydrate complex is acceptable so long as iron from the iron complex is released such that symptoms are treated. The single unit dose of iron carbohydrate complex can be administered parenterally, for example intravenously or intramuscularly. Intravenous administration can be delivered as a bolus or preferably as an infusion. For example, the single unit dose of iron carbohydrate complex can be intravenously infused at a concentration of about 1000 mg elemental iron in about 200 ml to about 300 ml of diluent, preferably about 215 ml of diluent or about 250 ml of diluent. The iron carbohydrate complex can be intravenously injected as a bolus. For example, the iron carbohydrate complex can be intravenously injected as a bolus at a concentration of about 1000 mg elemental iron in about 200 ml to about 300 ml of diluent, preferably about 215 ml of diluent or about 250 ml of diluent. The iron carbohydrate complex can be intramuscularly infused at a concentration of, for example, about 1000 mg elemental iron in about 200 ml to about 300 ml of diluent, preferably, about 250 ml of diluent or about 215 ml of diluent.

If applied as an infusion, the iron carbohydrate complex can be diluted with sterile saline (e.g., polynuclear iron (III)-hydroxide 4(R)-(poly-(1→4)-O-α-glucopyranosyl)-oxy-2(R),3(S),5(R),6-tetrahydroxy-hexanoate ("VIT-45") 0.9% mN NaCl or 500 mg iron in up to 250 mL NaCl). The iron carbohydrate complex can be intravenously injected as a bolus without dilution. As an example, the iron carbohydrate complex can be intramuscularly injected at a concentration of about 500 mg elemental iron in less than about 10 ml diluent, preferably about 5 ml.

Generally, total iron dosage will depend on the iron deficit of the patient. One skilled in the art can tailor the total iron dose required for a subject while avoiding iron overload, as overdosing with respect to the total required amount of iron has to be avoided, as is the case for all iron preparations.

The total iron dosage can be delivered as a single unit dosage or a series of single unit dosages. An appropriate single unit dosage level will generally be at least 0.6 grams of elemental iron, particularly at least 0.7 grams; at least 0.8 grams; at least 0.9 grams; at least 1.0 grams; at least 1.1 grams; at least 1.2 grams; at least 1.3 grams; at least 1.4 grams; at least 1.5 grams; at least 1.6 grams; at least 1.7 grams; at least 1.8 grams; at least 1.9 grams; at least 2.0 grams; at least 2.1 grams; at least 2.2 grams; at least 2.3 grams; at least 2.4 grams; or at least 2.5 grams. For example, a single unit dosage is at least 1.0 grams of elemental iron. As another example, a single unit dosage is at least 1.5 grams of elemental iron. As a further example, a single unit dosage is at least 2.0 grams of elemental iron. In yet another example, a single unit dosage is at least 2.5 grams of elemental iron.

An appropriate single unit dosage level can also be determined on the basis of patient weight. For example, an appropriate single unit dosage level will generally be at least 9 mg of elemental iron per kg body weight, particularly at least 10.5 mg/kg, at least 12 mg/kg, at least 13.5 mg/kg, at least 15 mg/kg, at least 16.5 mg/kg, at least 18 mg/kg, at least 19.5 mg/kg, at least 21 mg/kg, at least 22.5 mg/kg, at least 24 mg/kg, at least 25.5 mg/kg, at least 27 mg/kg, at least 28.5 mg/kg, at least 30 mg/kg, at least 31.5 mg/kg, at least 33 mg/kg, at least 34.5 mg/kg, at least 36 mg/kg, or at least 37.5 mg/kg.

Preferably, a single unit dosage can be administered in 15 minutes or less. For example, the single unit dosage can be administered in 14 minutes or less, 13 minutes or less, 12 minutes or less, 11 minutes or less, 10 minutes or less, 9 minutes or less, 8 minutes or less, 7 minutes or less, 6 minutes or less, 5 minutes or less, 4 minutes or less, 3 minutes or less, or 2 minutes or less.

Administration of iron can occur as a one-time delivery of a single unit dose or over a course of treatment involving delivery of multiple single unit doses. Multiple single unit doses can be administered, for example, over pre-determined time intervals or in response to the appearance and reappearance of symptoms. The frequency of dosing depends on the disease or disorder being treated, the response of each individual patient, and the administered amount of elemental iron. An appropriate regime of dosing adequate to allow the body to absorb the iron from the bloodstream can be, for example, a course of therapy once every day to once every eighteen months.

Such consecutive single unit dosing can be designed to deliver a relatively high total dosage of iron over a relatively low period of time. For example, a single unit dose (e.g., 1000 mg) can be administered every 24 hours. As illustration, a total dose of 2000, 2500, 3000, 3500, 4000, 4500, or 5000 mg of elemental iron can be delivered via consecutive daily single unit doses of about 600 mg to about 1000 mg of elemental iron. Given that a single unit dose of 1000 mg can be intravenously introduced into a patient in a concentrated form over, for example, two minutes, such administrative protocol provides a practitioner and patient with an effective, efficient, and safe means to deliver elemental iron.

As another example, a single unit dose can be administered every 3-4 days. As a further example, a single unit dose can be administered once per week. Alternatively, the single unit doses of iron complex may be administered ad hoc, that is, as symptoms reappear, as long as safety precautions are regarded as practiced by medical professionals.

It will be understood, however, that the specific dose and frequency of administration for any particular patient may be varied and depends upon a variety of factors, including the activity of the employed iron complex, the metabolic stability and length of action of that complex, the age, body weight, general health, sex, diet, mode and time of administration, rate of excretion, drug combination, the severity and nature of the particular condition, and the host undergoing therapy.

The following provides but a few examples of treatment protocols for various diseases or disorders.

Iron carbohydrate complex can be given as a single unit dose for the treatment of Restless Leg Syndrome. For example, 1000 mg of elemental iron from an iron carboxymaltose (e.g., polynuclear iron (III)-hydroxide 4(R)-(poly-(1→4)-O-α-glucopyranosyl)-oxy-2(R),3(S),5(R),6-tetrahydroxy-hexanoate) can be intravenously injected as a single dose (e.g., 1.5-5 mg iron/ml in normal saline) to a subject suffering from Restless Leg Syndrome. A single intravenous treatment can provide relief of symptoms for an extended period of time, approximately two to twelve months, although relief may be granted for shorter or longer periods. See U.S. Patent Pub. No. 2004/0180849, incorporated herein by reference. If desired, post-infusion changes in central nervous system iron status can be monitored using measurements of cerebral spinal fluid (CSF) ferritin (and other iron-related proteins) and of brain iron stores using MRI. Post-infusion changes in Restless Leg Syndrome are assessed using standard subjective (e.g., patient diary, rating scale) and objective (e.g., P50, SIT, Leg Activity Meters) measures of clinical status. If desired, to better evaluate RLS symptom amelioration, CSF and serum iron values, MRI measures of brain iron and full clinical evaluations with sleep and immobilization tests are obtained prior to treatment, approximately two weeks after treatment, and again twelve months later or when symptoms return. Clinical ratings, Leg Activity Meter recordings and serum ferritin are obtained monthly after treatment. CSF ferritin changes can also be used to assess symptom dissipation.

Iron carbohydrate complex can be given as a single unit dose for the treatment of iron deficiency anemia secondary to heavy uterine bleeding. For example, a single unit dose of 1,000 mg of elemental iron from an iron carboxymaltose in about 250 cc normal saline can be intravenously injected into a subject suffering from iron deficiency anemia secondary to heavy uterine bleeding over 15 minutes every week until a calculated iron deficit dose has been administered. The iron deficit dose can be calculated as follows:

If baseline *TSAT*<20% or Baseline Ferritin<50 ng/ml: Dose=Baseline weight (kg)×(15-Baseline *Hgb*[g/dL])×2.4+500 mg

OR

If baseline *TSAT*>20% and Baseline Ferritin>50 ng/mL: Dose=Baseline weight (kg)×(15-Baseline *Hgb*[g/dL])×2.4

(NOTE: Baseline Hgb equals the average of the last two central lab Hgb's)

Iron carbohydrate complex can be given as a single unit dose for the treatment of iron deficiency anemia. A subject diagnosed as suffering from iron deficiency anemia can be, for example, intravenously injected with a dose of 1,000 mg of iron as VIT-45 (or 15 mg/kg for weight<66 kg) in 250 cc of normal saline over 15 minutes. Subjects with iron deficiency anemia secondary to dialysis or non-dialysis dependent-Chronic Kidney Disease (CKD) as per K/DOQI guidelines will generally have Hgb<12 g/dL; TSAT<25%; and Ferritin<300 ng/mL. Subjects with iron deficiency anemia secondary to Inflammatory Bowel Disease will generally have Hgb<12 g/dL; TSAT<25%; and Ferritin<300 ng/mL. Subjects with iron deficiency anemia secondary to other conditions will generally have Hgb<12 g/dL; TSAT<25%; and Ferritin<100 ng/mL.

Subject in Need Thereof

Single unit dosages of intravenous iron described herein can be administered to a subject where there is a clinical need to deliver iron rapidly or in higher doses and/or in subjects with functional iron deficiency such as those on erythropoietin therapy. A determination of the need for treatment with parenteral iron is within the abilities of one skilled in the art. For example, need can be assessed by monitoring a patient's iron status. The diagnosis of iron deficiency can be based on appropriate laboratory tests, for example, haemoglobin (Hb), serum ferritin, serum iron, transferrin saturation (TfS), and hypochromic red cells.

A determination of the need for treatment with high dosages of parenteral iron can be also be determined through diagnosis of a patient as suffering from a disease, disorder, or condition that is associated with iron deficiency or dysfunctional iron metabolism. For example, many chronic renal failure patients receiving erythropoietin will require intravenous iron to maintain target iron levels. As another example, most hemodialysis patients will require repeated intravenous iron administration, due to dialysis-associated blood loss and resulting negative iron balance.

Monitoring frequency can depend upon the disease, disorder, or condition the patient is afflicted with or at risk for. For example, in a patient initiating erythropoietin therapy, iron indices are monitored monthly. As another example, in patients who have achieved target range Hb or are receiving intravenous iron therapy, TSAT and ferritin levels can be monitored every 3 months.

A patient's iron status can be indicative of an absolute or a functional iron deficiency, both of which can be treated with the compositions and methods described herein. An absolute iron deficiency occurs when an insufficient amount of iron is available to meet the body's requirements. The insufficiency may be due to inadequate iron intake, reduced bioavailability of dietary iron, increased utilization of iron, or chronic blood loss. Prolonged iron deficiency can lead to iron deficiency anemia—a microcytic, hypochromic anemia in which there are inadequate iron stores. Absolute iron deficiency is generally indicated where TSAT<20% and Ferritin<100 ng/mL.

Functional iron deficiency can occur where there is a failure to release iron rapidly enough to keep pace with the demands of the bone marrow for erythropoiesis, despite adequate total body iron stores. In these cases, ferritin levels may be normal or high, but the supply of iron to the erythron is limited, as shown by a low transferrin saturation and an increased number of microcytic, hypochromic erythrocytes. Functional iron deficiency can be characterized by the following characteristics: Inadequate hemoglobin response to erythropoietin; Serum ferritin may be normal or high; Transferrin saturation (TSAT) usually <20%; and/or reduced mean corpuscular volume (MCV) or mean corpuscular hemoglobin concentration (MCHC) in severe cases. Functional iron deficiency (i.e., iron stores are thought to be adequate but unavailable for iron delivery) is generally indicated where TSAT<20% and Ferritin>100 ng/mL.

Assessing the need for intravenous iron therapy as described herein can be according to the National Kidney Foundation's Kidney Disease Outcomes Quality Initiative. See NKF-K/DOQI, Clinical Practice Guidelines for Anemia of Chronic Kidney Disease (2000); Am J Kidney Dis (2001) 37(supp 1), S182-S238. The DOQI provides optimal clinical practices for the treatment of anemia in chronic renal failure. The DOQI guidelines specify intravenous iron treatment of kidney disease based on hemoglobin, transferrin saturation (TSAT), and ferritin levels.

Assessment of need for intravenous iron therapy can also be according to a patient's target iron level. For example, the target hemoglobin level of a patient can be selected as 11.0 g/dL to 12.0 g/dL (hematocrit approximately 33% to 36%). To achieve target hemoglobin with optimum erythropoietin doses, sufficient iron, supplied via an iron carbohydrate complex, is provided to maintain TSAT≧20% and ferritin≧100 ng/mL. In erythropoietin-treated patients, if TSAT levels are below 20%, the likelihood that hemoglobin will rise or erythropoietin doses fall after iron administration is high. Achievement of target hemoglobin levels with optimum erythropoietin doses is associated with providing sufficient iron to maintain TSAT above 20%.

Iron therapy can be given to maintain target hemoglobin while preventing iron deficiency and also preventing iron overload. Adjusting dosage of iron to maintain target levels of hemoglobin, hematocrit, and laboratory parameters of iron storage is within the normal skill in the art. For example, where a patient is anemic or iron deficient, intravenous iron can be administered when a patient has a ferritin<800, a TSAT<50, and/or a Hemoglobin<12. Iron overload can be avoided by withholding iron for TSAT>50% and/or ferritin>800 ng/mL.

Where a patient is not anemic or iron deficient but is in need of iron administration, for example a patient suffering from Restless Leg Syndrome, hemoglobin and TSAT levels are not necessarily relevant, while ferritin>800 can still provides a general cut off point for administration.

Iron Carbohydrate Complex

Iron carbohydrate complexes are commercially available, or have well known syntheses. Examples of iron carbohydrate complexes include iron monosaccharide complexes, iron disaccharide complexes, iron oligosaccharide complexes, and iron polysaccharide complexes, such as: iron carboxymaltose, iron sucrose, iron polyisomaltose (iron dextran), iron polymaltose (iron dextrin), iron gluconate, iron sorbitol, iron hydrogenated dextran, which may be further complexed with other compounds, such as sorbitol, citric acid and gluconic acid (for example iron dextrin-sorbitol-citric acid complex and iron sucrose-gluconic acid complex), and mixtures thereof.

Applicants have discovered that certain characteristics of iron carbohydrate complexes make them amenable to administration at dosages far higher than contemplated by current administration protocols. Preferably, iron carbohydrate complexes for use in the methods described herein are those which have one or more of the following characteristics: a nearly neutral pH (e.g., about 5 to about 7); physiological osmolarity; stable carbohydrate component; an iron core size no greater than about 9 nm; mean diameter particle size no greater than about 35 nm, preferably about 25 nm to about 30 nm; slow and competitive delivery of the complexed iron to endogenous iron binding sites; serum half-life of over about 7 hours; low toxicity; non-immunogenic carbohydrate component; no cross reactivity with anti-dextran antibodies; and/or low risk of anaphylactoid/hypersensitivity reactions.

It is within the skill of the art to test various characteristics of iron carbohydrate complexes as so determine amenability to use in the methods described herein. For example, pH and osmolarity are straightforward determinations performed on a sample formulation. Likewise, techniques such as electron micrograph imaging, transmission electron microscopy, and atomic force microscopy provide direct methods to analyze both iron core and particle size. See e.g., FIG. 1; Table 1. The stability of the carbohydrate complex can be assessed through physicochemical properties such as kinetic characteristics, thermodynamic characteristics, and degradation kinetics. See Geisser et al., Arzneimittelforschung (1992) 42(12), 1439-1452. Useful techniques to assess physical and electronic properties include absorption spectroscopy, X-ray diffraction analysis, transmission electron microscopy, atomic force microscopy, and elemental analysis. See Kudasheva et al. (2004) J Inorg Biochem 98, 1757-1769. Pharmacokinetics can be assessed, for example, by iron tracer experiments. Hypersensitivity reactions can be monitored and assessed as described in, for example, Bailie et al. (2005) Nephrol Dial Transplant, 20(7), 1443-1449. Safety, efficacy, and toxicity in human subjects can be assessed, for example, as described in Spinowitz et al. (2005) Kidney Intl 68, 1801-1807.

A particularly preferred iron carbohydrate complex will have a pH between 5.0-7.0; physiological osmolarity; an iron core size no greater than 9 nm; mean diameter particle size no greater than 30 nm; serum half-life of over 10 hours; a non-immunogenic carbohydrate component; and no cross reactivity with anti-dextran antibodies. One example of a preferred iron carbohydrate complex for use in the methods described herein is an iron carboxy-maltose complex (e.g., polynuclear iron (III)-hydroxide 4(R)-(poly-(1→4)-O-α-glucopyranosyl)-oxy-2(R),3(S),5(R),6-tetrahydroxy-hexanoate, "VIT-45"). Another example of a preferred iron carbohydrate complex for use in the methods described herein is a carboxyalkylated reduced polysaccharide iron oxide complex (e.g., ferumoxytol, described in U.S. Pat. No. 6,599,498).

Preferably, an iron carbohydrate complex, for use in methods disclosed herein, contains about 24% to about 32% elemental iron, more preferably about 28% elemental iron. Preferably, an iron carbohydrate complex, for use in methods disclosed herein, contains about 25% to about 50% carbohydrate (e.g., total glucose). Preferably, an iron carbohydrate complex, for use in methods disclosed herein, is about 90,000 daltons to about 800,000 daltons, more preferably 100,000 daltons to about 350,000 daltons.

Iron Carboxymaltose Complex

One preferred iron carbohydrate complex for use in the methods described herein is an iron carboxymaltose complex. An example of an iron carboxymaltose complex is polynuclear iron (III)-hydroxide 4(R)-(poly-(1→4)-O-α-glucopyranosyl)-oxy-2(R),3(S),5(R),6-tetrahydroxy-hexanoate ("VIT-45"). VIT-45 is a Type I polynuclear iron (III) hydroxide carbohydrate complex that can be administered as parenteral iron replacement therapy for the treatment of various anemia-related conditions as well as other iron-metabolism related conditions. VIT-45 can be represented by the chemical formula: [FeOx(OH)y(H2O)z]n[{(C6H10O5)m (C6H12O7)}l]k, where n is about 103, m is about 8, l is about 11, and k is about 4). The molecular weight of VIT-45 is about 150,000 Da. An exemplary depiction of VIT-45 is provided in FIG. 2.

The degradation rate and physicochemical characteristics of the iron carbohydrate complex (e.g., VIT-45) make it an efficient means of parenteral iron delivery to the body stores. It is more efficient and less toxic than the lower molecular weight complexes such as iron sorbitol/citrate complex, and does not have the same limitations of high pH and osmolarity that leads to dosage and administration rate limitations in the case of, for example, iron sucrose and iron gluconate.

The iron carboxymaltose complex (e.g., VIT-45) generally does not contain dextran and does not react with dextran antibodies; therefore, the risk of anaphylactoid/hypersensitivity reactions is very low compared to iron dextran. The iron carboxymaltose complex (e.g., VIT-45) has a nearly neutral pH (5.0 to 7.0) and physiological osmolarity, which makes it possible to administer higher single unit doses over shorter time periods than other iron-carbohydrate complexes. The iron carboxymaltose complex (e.g., VIT-45) can mimic physiologically occurring ferritin. The carbohydrate moiety of iron carboxymaltose complex (e.g., VIT-45) is metabolized by the glycolytic pathway. Like iron dextran, the iron carboxymaltose complex (e.g., VIT-45) is more stable than iron gluconate and sucrose. The iron carboxymaltose complex (e.g., VIT-45) produces a slow and competitive delivery of the complexed iron to endogenous iron binding sites resulting in an acute toxicity one-fifth that of iron sucrose. These characteristics of the iron carboxymaltose complex (e.g., VIT-45) allow administration of higher single unit doses over shorter periods of time than, for example, iron gluconate or iron sucrose. Higher single unit doses can result in the need for fewer injections to replete iron stores, and consequently is often better suited for outpatient use.

After intravenous administration, the iron carboxymaltose complex (e.g., VIT-45) is mainly found in the liver, spleen, and bone marrow. Pharmacokinetic studies using positron emission tomography have demonstrated a fast initial elimination of radioactively labeled iron (Fe) $^{52}$Fe/$^{59}$Fe VIT-45 from the blood, with rapid transfer to the bone marrow and rapid deposition in the liver and spleen. See e.g., Beshara et al. (2003) Br J Haematol 2003; 120(5): 853-859. Eight hours after administration, 5 to 20% of the injected amount was observed to be still in the blood, compared with 2 to 13% for iron sucrose. The projected calculated terminal half-life ($t_{1/2}$) was approximately 16 hours, compared to 3 to 4 days for iron dextran and 6 hours for iron sucrose.

The iron in the iron carboxymaltose complex (e.g., VIT-45) slowly dissociates from the complex and can be efficiently used in the bone marrow for Hgb synthesis. Under VIT-45 administration, red cell utilization, followed for 4 weeks, ranged from 61% to 99%. Despite the relatively higher uptake by the bone marrow, there was no saturation of marrow transport systems. Thus, high red cell utilization of iron carboxymaltose complex occurs in anemic patients. In addition, the reticuloendothelial uptake of this complex reflects the safety of polysaccharide complexes. Non-saturation of transport systems to the bone marrow indicated the presence of a large interstitial transport pool (e.g., transferrin).

Other studies in patients with iron deficiency anemia revealed increases in exposure roughly proportional with VIT-45 dose (maximal total serum iron concentration was approximately 150 µg/mL and 320 µg/mL following 500 mg and 1000 mg doses, respectively). In these studies, VIT-45 demonstrated a monoexponential elimination pattern with a $t_{1/2}$ in the range 7 to 18 hours, with negligible renal elimination.

Single-dose toxicity studies have demonstrated safety and tolerance in rodents and dogs of intravenous doses of an iron carboxymaltose complex (VIT-45) up to 60 times more than the equivalent of an intravenous infusion of 1,000 mg iron once weekly in humans. Pre-clinical studies in dogs and rats administered VIT-45 in cumulative doses up to 117 mg iron/kg body weight over 13 weeks showed no observed adverse effect level in dose-related clinical signs of iron accumulation in the liver, spleen, and kidneys. No treatment-related local tissue irritation was observed in intra-arterial, perivenous, or intravenous tolerance studies in the rabbit. In vitro and in vivo mutagenicity tests provided no evidence that VIT-45 is clastogenic, mutagenic, or causes chromosomal damage or bone marrow cell toxicity. There were no specific responses to VIT-45 in a dextran antigenicity test.

Approximately 1700 subjects have been treated with an iron carboxymaltose complex (VIT-45) in open label clinical trials (see e.g., Example 5). Many of these subjects have received at least one dose of 15 mg/kg (up to a maximum dose of 1,000 mg) of VIT-45 over 15 minutes intravenously. Few adverse events and no serious adverse events or withdrawals due to adverse events related to VIT-45 administration have been reported. No clinically relevant adverse changes in safety laboratories have been seen.

The physicochemical characteristics of the iron carboxymaltose complex (e.g., VIT-45), the pattern of iron deposition, and the results of the above described studies demonstrate that iron carboxymaltose complex can be safely administered at high single unit therapeutic doses as described herein.

Polyglucose sorbitol carboxymethyl ether-coated non-stoichiometric magnetite

Another preferred iron carbohydrate complex for use in the methods described herein is a polyglucose sorbitol carboxymethyl ether-coated non-stoichiometric magnetite (e.g., "ferumoxytol"). Ferumoxytol is known in the art to be effective for treating anemia (at single unit doses lower than described herein). See e.g., Spinowitz et al. (2005) Kidney Intl 68, 1801-1807. Ferumoxytol is a superparamagnetic iron oxide that is coated with a low molecular weight semi-synthetic carbohydrate, polyglucose sorbitol carboxymethyl ether. Ferumoxytol and its synthesis are described in U.S. Pat. No. 6,599,498, incorporated herein by reference. Safety, efficacy, and pharmacokinetics of ferumoxytol are as described, for example, in Landry et al. (2005) Am J Nephrol 25, 400-410, 408; and Spinowitz et al. (2005) Kidney Intl 68, 1801-1807.

The iron oxide of ferumoxytol is a superparamagnetic form of non-stoichiometric magnetite with a crystal size of 6.2 to 7.3 nm. Average colloidal particle size can be about 30 nm, as determined by light scattering. Molecular weight is approximately 750 kD. The osmolarity of ferumoxytol is isotonic at 297 mOsm/kg and the pH is neutral. The blood half-life of ferumoxytol is approximately 10-14 hours. It has been previously reported that ferumoxytol can be given by direct intravenous push over 1-5 minutes in doses up to 1,800 mg elemental iron per minute, with maximal total dose up to 420 mg per injection. Landry et al. (2005) Am J Nephrol 25, 400-410, 408.

Core and Particle Size

Intravenous iron agents are generally spheroidal iron-carbohydrate nanoparticles. At the core of each particle is an iron-oxyhydroxide gel. The core is surrounded by a shell of carbohydrate that stabilizes the iron-oxyhydroxide, slows the release of bioactive iron, and maintains the resulting particles in colloidal suspension. Iron agents generally share the same core chemistry but differ from each other by the size of the core and the identity and the density of the surrounding carbohydrate. See Table 1; FIG. 1.

TABLE 1

Core and Particle Size of Iron Carbohydrate Complexes

| | Iron (III) Control Release Test | Size of the Particle (nm) +/− SEM | |
|---|---|---|---|
| | $T_{75}$ (min) | Iron core | Total Particle |
| Dexferrum (an iron dextran) | 122.5 | 11.8 ± 4 | 27 ± 6 |
| VIT-45 (an iron carboxymaltose) | 117.8 | 4.4 ± 1.4 | 6.7 ± 2.5 |
| Venofer (an iron sucrose) | 10.2 | 2.8 ± 1 | 6.5 ± 4 |

Differences in core size and carbohydrate chemistry can determine pharmacological and biological differences, including clearance rate after injection, iron release rate in vitro, early evidence of iron bioactivity in vivo, and maximum tolerated dose and rate of infusion.

One of the primary determinants of iron bioactivity is the size of the core and the surface area to volume ratio. Generally, the rate of labile iron release in each agent is inversely related to the size of its iron core. Van Wyck (2004) J. Am. Soc. Nephrology 15, S107-S111, S109. Furthermore, in vitro iron donation to transferrin is inversely related to core size. Core size can depend upon the number of iron atoms contained within. For example, the number of iron atoms contained within a 1 nm core is calculated to be 13, while a 10 nm core is calculated to contain 12770 iron atoms. Where agents share the same core chemistry, the rate of iron release per unit surface area is likely similar, differing perhaps by the strength of the carbohydrate ligand-core iron bound. But for the same total amount of core iron, surface area available for iron release increases dramatically as core radius decreases. That is to say, for equal amounts of iron, the smaller the core, the greater the surface area available for iron release. Of course, the explanation for this non-linear trend is the fact that volume is radius cubed. In short, a collection of many small spheres exposes a greater total surface area than does a collection of an equal mass of fewer, larger spheres.

A smaller iron core size of an iron complex administered for the treatment of various diseases, disorders, or conditions allows wider distribution through tissues, a greater rate of labile iron release, and increased in vitro iron donation to transferrin. Furthermore, the iron complex is more evenly distributed and metabolizes faster due to the smaller core size. But if the core size is too small, the iron complex can move into cells unable to metabolize iron. In one embodiment, an iron complex with a mean iron core size of no greater than about 9 nm is administered. In various embodiments, mean iron core size is less than about 9 nm but greater than about 1 nm, about 2 nm, about 3 nm, about 4 nm, about 5 nm, about 6 nm, about 7 nm, or about 8 nm. Mean iron core size can be, for example, between about 1 nm and about 9 nm; between about 3 nm and about 7 nm; or between about 4 nm and about 5 nm.

The molecular weight (i.e., the whole molecular weight of the agent) is considered a primary determinant in the pharmacokinetics, or in other words, how quickly it is cleared from the blood stream. The amount of labile (i.e., biologicaly available) iron is inversely correlated with the molecular weight of the iron-carbohydrate complex. Van Wyck (2004) J. Am. Soc. Nephrology 15, S107-S111, S109. That is to say, the magnitude of labile iron effect is greatest in iron-carbohydrate compounds of lowest molecular weight and least in those of the highest molecular weight. Generally, there is a direct relationship between the molecular weight of the agent and the mean diameter of the entire particle (i.e., the iron core along with the carbohydrate shell). In various embodiments, the mean diameter size of a particle of the iron carbohydrate complex is no greater than about 35 nm. For example, the particle mean size can be no greater than about 30 nm. As another example, the particle mean size can be no greater than about 25 nm. As another example, the particle mean size can be no greater than about 20 nm. As another example, the particle mean size can be no greater than about 15 nm. As a further example, the particle mean size can be no greater than about 10 nm. As another example, the particle mean size can be no greater than about 7 nm.

Absence of Significant Adverse Reaction to the Single Dosage Unit Administration Generally, a safe and effective amount of an iron carbohydrate complex is, for example, that amount that would cause the desired therapeutic effect in a patient while minimizing undesired side effects. The dosage regimen will be determined by skilled clinicians, based on factors such as the exact nature of the condition being treated, the severity of the condition, the age and general physical condition of the patient, and so on. Generally, treatment-emergent adverse events will occur in less than about 5% of treated patients. For example, treatment-emergent adverse events will occur in less than 4% or 3% of treated patients. Preferably, treatment-emergent adverse events will occur in less than about 2% of treated patients.

For example, minimized undesirable side effects can include those related to hypersensitivity reactions, sometimes classified as sudden onset closely related to the time of dosing, including hypotension, bronchospasm, layngospasm, angioedema or uticaria or several of these together. Hypersensitivity reactions are reported with all current intravenous iron products independent of dose. See generally Bailie et al. (2005) Nephrol Dial Transplant, 20(7), 1443-1449. As another example, minimized undesirable side effects can include those related to labile iron reactions, sometimes classified as nausea, vomiting, cramps, back pain, chest pain, and/or hypotension. Labile iron reactions are more common with iron sucrose, iron gluconate, and iron dextran when doses are large and given fast.

Pharmaceutical Formulations

In many cases, a single unit dose of iron carbohydrate complex may be delivered as a simple composition comprising the iron complex and the buffer in which it is dissolved. However, other products may be added, if desired, for example, to maximize iron delivery, preservation, or to optimize a particular method of delivery.

A "pharmaceutically acceptable carrier" includes any and all solvents, dispersion media, coatings, antibacterial and anti-fungal agents, isotonic and absorption delaying agents, and the like, compatible with pharmaceutical administration (see e.g., Banker, Modern Pharmaceutics, Drugs and the Pharmaceutical Sciences, 4th ed. (2002) ISBN 0824706749; Remington The Science and Practice of Pharmacy, 21st ed. (2005) ISBN 0781746736). Preferred examples of such carriers or diluents include, but are not limited to, water, saline, Finger's solutions and dextrose solution. Supplementary active compounds can also be incorporated into the compositions. For intravenous administration, the iron carbohydrate complex is preferably diluted in normal saline to approximately 2-5 mg/ml. The volume of the pharmaceutical solution is based on the safe volume for the individual patient, as determined by a medical professional.

An iron complex composition of the invention for administration is formulated to be compatible with the intended route of administration, such as intravenous injection. Solutions and suspensions used for parenteral, intradermal or subcutaneous application can include a sterile diluent, such as water for injection, saline solution, polyethylene glycols, glycerine, propylene glycol or other synthetic solvents; antibacterial agents such as benzyl alcohol or methyl parabens; antioxidants such as ascorbic acid or sodium bisulfite; buffers such as acetates, citrates or phosphates, and agents for the adjustment of tonicity such as sodium chloride or dextrose. The pH can be adjusted with acids or bases, such as hydrochloric acid or sodium hydroxide. Preparations can be enclosed in ampules, disposable syringes or multiple dose vials made of glass or plastic.

Pharmaceutical compositions suitable for injection include sterile aqueous solutions or dispersions for the extemporaneous preparation of sterile injectable solutions or dispersion. For intravenous administration, suitable carriers include physiological saline, bacteriostatic water, Cremophor EL™ (BASF; Parsippany, N.J.) or phosphate buffered saline (PBS). The composition must be sterile and should be fluid so as to be administered using a syringe. Such compositions should be stable during manufacture and storage and must be preserved against contamination from microorganisms, such as bacteria and fungi. The carrier can be a dispersion medium containing, for example, water, polyol (such as glycerol, propylene glycol, and liquid polyethylene glycol), and other compatible, suitable mixtures. Various antibacterial and anti-fungal agents, for example, parabens, chlorobutanol, phenol, ascorbic acid, and thimerosal, can contain microorganism contamination. Isotonic agents such as sugars, polyalcohols, such as manitol, sorbitol, and sodium chloride can be included in the composition. Compositions that can delay absorption include agents such as aluminum monostearate and gelatin.

Sterile injectable solutions can be prepared by incorporating an iron complex in the required amount in an appropriate solvent with a single or combination of ingredients as required, followed by sterilization. Methods of preparation of sterile solids for the preparation of sterile injectable solutions include vacuum drying and freeze-drying to yield a solid containing the iron complex and any other desired ingredient.

Active compounds may be prepared with carriers that protect the compound against rapid elimination from the body, such as a controlled release formulation, including implants and microencapsulated delivery systems. Biodegradable or biocompatible polymers can be used, such as ethylene vinyl acetate, polyanhydrides, polyglycolic acid, collagen, polyorthoesters, and polylactic acid. Such materials can be obtained commercially from ALZA Corporation (Mountain View, Calif.) and NOVA Pharmaceuticals, Inc. (Lake Elsinore, Calif.), or prepared by one of skill in the art.

A single unit dose of iron carbohydrate complex may be intravenously administered in a volume of pharmaceutically acceptable carrier of, for example, about 1000 mg of elemental iron in about 200 ml to about 300 ml of diluent. For example, a single unit dose of iron carbohydrate complex may be intravenously administered in a volume of pharmaceutically acceptable carrier of about 1000 mg of elemental iron in about 250 ml of diluent. As another example, a single unit dose of iron carbohydrate complex may be intravenously administered in a volume of pharmaceutically acceptable carrier of about 1000 mg of elemental iron in about 215 ml of diluent.

A preferred pharmaceutical composition for use in the methods described herein contains VIT-45 as the active pharmaceutical ingredient (API) with about 28% weight to weight (m/m) of iron, equivalent to about 53% m/m iron (III)-hydroxide, about 37% m/m of ligand, <6% m/m of NaCl, and <10% m/m of water.

Kits for Pharmaceutical Compositions

Iron complex compositions can be included in a kit, container, pack or dispenser, together with instructions for administration according to the methods described herein. When the invention is supplied as a kit, the different components of the composition may be packaged in separate containers, such as ampules or vials, and admixed immediately before use. Such packaging of the components separately may permit long-term storage without losing the activity of the components. Kits may also include reagents in separate containers that facilitate the execution of a specific test, such as diagnostic tests.

The reagents included in kits can be supplied in containers of any sort such that the life of the different components are preserved and are not adsorbed or altered by the materials of the container. For example, sealed glass ampules or vials may contain lyophilized iron complex or buffer that have been packaged under a neutral non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include bottles that are fabricated from similar substances as ampules, and envelopes that consist of foil-lined interiors, such as aluminum or an alloy. Other containers include test tubes, vials, flasks, bottles, syringes, etc. Containers may have a sterile access port, such as a bottle having a stopper that can be pierced by a hypodermic injection needle. Other containers may have two compartments that are separated by a readily removable membrane that, upon removal, permits the components to mix. Removable membranes may be glass, plastic, rubber, etc.

Kits may also be supplied with instructional materials. Instructions may be printed on paper or other substrate, and/or may be supplied on an electronic-readable medium, such as a floppy disc, CD-ROM, DVD-ROM, mini-disc, SACD, Zip disc, videotape, audio tape, etc. Detailed instructions may not be physically associated with the kit; instead, a user may be directed to an internet web site specified by the manufacturer or distributor of the kit, or supplied as electronic mail.

Having described the invention in detail, it will be apparent that modifications, variations, and equivalent embodiments are possible without departing the scope of the invention defined in the appended claims. It should be understood that all references cited are incorporated herein by reference. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Non-Toxicity Studies

Nonclinical toxicity of VIT-45 is very low, as is normal for Type I polynuclear iron (III)-hydroxide carbohydrate complexes. The single dose toxicity is so low that the $LD_{50}$ could not be estimated and is higher than 2000 mg iron/kg b.w. Mice tested with a single dose of 250 mg iron/kg b.w., injected within 2 seconds, showed no signs of illness. The highest non-lethal dose level of 1000 mg iron/kg b.w. in mice and rats is also very high in comparison to a single unit dose of, for example, 15 mg iron/kg b.w. once per week in humans. These results provide factors of about 70-fold a human dose, demonstrating a large safety margin for acute toxicity of the product.

Example 2

Pharmokinetic Studies

Pharmacokinetic and red blood cell measurements of $^{52}$Fe/$^{59}$Fe labelled VIT-45 following i.v. administration using PET in 6 patients showed a red blood cell utilization from 61 to 99%. The 3 patients with iron deficiency anemia showed a utilization of radiolabelled iron of 91 to 99% after 24 days, compared to 61 to 84% for 3 patients with renal anaemia. The terminal $t_{1/2}$ for VIT-45 was calculated to be approximately 16 hours, compared to about 6 hours for iron sucrose. In two further studies in patients with iron deficiency anemia, pharmacokinetic analyses revealed increases in exposure roughly proportional with VIT-45 dose (Cmax approximately 150 µg/mL and 320 µg/mL following 500 mg and 1000 mg doses, respectively). VIT-45 demonstrated a monoexponential elimination pattern with a $t_{1/2}$ in the range 7 to 18 hours. There was negligible renal elimination.

Example 3

Efficacy Studies

The main pharmacodynamic effects of VIT-45 were transient elevations of serum iron levels, TfS and serum ferritin. These effects were seen in all studies (where measured), following both single doses and repeated doses. The increase in serum ferritin levels illustrated the replenishment of the depleted iron stores, which is a well-identified and desired effect of iron therapy. In addition, transiently elevated TfS indicated that iron binding capacity was almost fully utilized following VIT-45 infusion.

Efficacy of iron replacement therapy is interpreted mainly in terms of the ability to normalise Hb levels and iron stores. In the multiple dose studies, patients demonstrated a slowly-developing, sustained increase in Hb levels during study participation. In one study, 37% and 48% of patients in Cohorts 1 and 2, respectively, had achieved normal Hb levels at the 4-week follow-up visit, and 75% and 73%, respectively, had achieved a $\geq$20 g/L increase in Hb on at least 1 occasion.

In another study (patients receiving regular haemodialysis), the majority of patients (61.7%) achieved an increase of Hb of $\geq$10 g/L at any point during the study. Serum ferritin and TfS levels showed a more prolonged elevation following repeated VIT-45 infusions, indicating a sustained replenishment of iron stores. However, elevated levels of ferritin and TfS indicating iron overload were avoided. In both of these studies, there was a gradual decrease in transferrin over time, also indicating successful iron replacement.

Example 4

Safety Assessments

Safety assessments were made in 73 patients with iron deficiency anemia (27 single-dose, 46 repeated-dose), and 166 patients with renal anaemia (3 single-dose, 163 repeated-dose) who received VIT-45 at individual iron doses of 100 mg up to 1000 mg (cumulative doses of 100 to 2200 mg). These studies showed a safety profile equal to, or exceeding, currently available parenteral iron formulations.

In the single-dose studies, there were few adverse events and no serious adverse events or withdrawals due to adverse events. There were also no related clinically relevant adverse changes in vital signs, 12-lead ECGs or laboratory safety tests.

In the repeated-dose studies, there were no deaths attributed to VIT-45, while 10 patients experienced serious adverse events. All of these cases occurred in patients with renal anaemia receiving haemodialysis and were considered not related to the VIT-45 treatment. Very few patients were withdrawn from the studies due to treatment-emergent adverse events, and only 2 withdrawals (due to allergic skin reactions) were considered possibly related to treatment. In each of the repeated-dose studies, no patients experienced clinically significant changes in 12-lead ECGs that were related to treatment. There were no consistent changes in laboratory safety parameters, although there was a low incidence (total 6 patients) of laboratory values reported as treatment-related treatment-emergent adverse events (elevated CRP, AST, ALT and GGT, abnormal liver function tests and elevated WBC).

Although many patients in these 2 studies had serum ferritin above 500 µg/L on at least 1 occasion during the study, very few patients also had TfS values >50%. Generally, the elevations of ferritin and TfS were of short duration. Iron overload was avoided using the dosing schedules defined in the studies.

Example 5

Integrated Safety Studies

The following example demonstrates the safety and effectiveness of parenteral VIT-45 in the treatment of anemia in a variety of patient populations, as determined from several integrated safety studies.

A total of 2429 subjects were treated with VIT-45 or control agents over 10 studies that provide safety data for VIT-45. Of these, 1709 subjects received VIT-45 (1095 in completed multicenter studies, 584 in placebo-controlled, single-dose, crossover studies and 30 in pharmacokinetic studies). The mean total dose of VIT-45 administered among the 1095 subjects in the completed multicenter studies was approximately 1300 mg; however, some subjects received VIT-45 doses as high as 3400 mg. The majority of the subjects treated were able to receive their calculated iron requirement in only 1 or 2 doses.

Table 2 provides a summary of VIT-45 studies described in this example.

Study A was a single-center, single-dose escalation, randomized, double-blind, placebo-controlled pharmacokinetic study. Subjects were male and female, between 18 and 45 years of age, inclusive, with mild iron-deficiency anemia. Treatment was a single IV bolus injection of VIT-45 at 100 mg, 500 mg, 800 mg, or 1000 mg. Examined pharmacokinetic parameters included total serum iron and pharmacodynamic (serum ferritin and transferrin, iron binding capacity, % TSAT post, hemoglobin, reticulocyte, and serum transferrin receptor concentrations) endpoints. Examined safety parameters included adverse events, clinical laboratory evaluations, vital signs, ECG, and physical examinations.

Study B was a single-center, single-dose, open label, uncontrolled pharmacokinetic study. Subjects were between 18 and 75 years of age with iron-deficiency or renal anemia with no other cause of anaemia. Inclusion criteria included hemoglobin concentration between 9 and 13 g/dL, no blood transfusions in the previous 3 months, and no history of treatment with intravenous iron in the last 2 weeks. Treatment was a single IV bolus injection of VIT-45 at 100 mg labelled with $^{52}$Fe and $^{59}$Fe. Examined primary pharmacokinetic parameters included the distribution of $^{52}$Fe and incorporation of $^{59}$Fe into red blood cells. Examined safety parameters included adverse events, clinical laboratory evaluations, vital signs, and physical examinations.

Study C was an open-label, multicenter, randomized, multiple-dose, active-controlled postpartum anemia study. Subjects were female, postpartum within 10 days after delivery, with hemoglobin≦10 g/dL at Baseline based on the average of 2 hemoglobin values drawn ≧18 hours postpartum. Treatment was once weekly doses of VIT-45 for six weeks. VIT-45 dosage was based on the calculated iron deficit (≦2500 mg total). Where screening serum transferrin saturation (TSAT) was ≦20% or screening ferritin was ≦50 ng/mL, dosage=pre-pregnancy weight (kg)×(15-baseline hemoglobin [g/dL])×2.4+500 mg. Where screening TSAT was >20% and screening ferritin was >50 ng/mL, dosage=pre-pregnancy weight (kg)×(15-baseline hemoglobin [g/dL])×2.4. Infusion of VIT-45 was as follows: ≦200 mg, administered as an undiluted intravenous push (IVP) over 1-2 minutes; 300-400 mg, administered in 100 cc normal saline solution (NSS) over 6 minutes; 500-1,000 mg administered in 250 cc NSS over 15 minutes. For primary efficacy, "success" was defined as an increase in hemoglobin of ≧2 g/dL anytime between baseline and end of study or time of intervention, while "failure" was defined as <2 g/dL increase in hemoglobin at all times between baseline and end of study or time of intervention. Examined safety parameters included adverse events, clinical laboratory evaluations, vital signs, and physical examinations.

Study D was a multicenter, open-label, randomized, active-controlled, multiple-dose postpartum anemia study. Subjects were adult women ≧18 years old with postpartum anaemia within 6 days after delivery. Treatment was administered once-weekly for a maximum of 3 infusions. Patients received IV infusions of 16.7 mL/min to deliver a maximum dose of 1000 mg iron per infusion. Patients received VIT-45 infusions once weekly for up to 3 occasions until the calculated cumulative dose was reached. Patients ≦66 kg received a minimum dose of 200 mg and a maximum dose of 15 mg iron/kg during each infusion. Patients >66 kg received a dose of 1000 mg on the first dosing occasion, and a minimum dose of 200 mg and a maximum dose of 1000 mg at each subsequent dosing. Doses of 200-400 mg were diluted in 100 cc NSS and 500-1000 mg were diluted in 250 cc NSS. Primary efficacy was examined as change from baseline levels of hemoglobin to Week 12. Examined safety parameters included adverse events in the mother and breast-fed infant, adverse events leading to discontinuation of treatment, vital signs, 12-lead electrocardiogram (ECG), physical examinations, and clinical laboratory panels.

Study E was a multicenter, open-label, randomized, active-controlled, multiple-dose hemodialysis-associated anemia study. Subjects were adult male or female subjects between the ages of 18 and 80 years (inclusive) requiring haemodialysis with iron deficiency secondary to chronic renal failure. Dosing started on Day 1, Week 0 for both treatment arms and continued 2 or 3 times weekly until the individual calculated cumulative dose was reached. Patients received 200 mg VIT-45 during their scheduled haemodialysis sessions (2-3 sessions/week) until the calculated cumulative dose was reached. Cumulative total iron requirement was calculated for each patient using the Ganzoni formula. Primary Efficacy was examined as the percentage of patients reaching an increase in hemoglobin>10 g/L at 4 weeks after baseline. Examined safety parameters included adverse events, vital signs, 12-lead ECG, physical examinations, and clinical laboratory evaluations.

Study F was a multicenter, open-label, multiple dose, uncontrolled hemodialysis-associated anemia study. Subjects were male and female patients 18-65 years of age, inclusive, with haemodialysis-associated anaemia undergoing maintenance haemodialysis. Treatment duration was a maximum of six weeks. Patients received 200 mg VIT-45 during their scheduled haemodialysis sessions (2-3 sessions/week) until the calculated cumulative dose was reached. Cumulative total iron requirement was calculated for each patient using the Ganzoni formula. Efficiency was examined as correction of iron deficiency and hemoglobin concentration of the patient. Examined safety parameters included adverse events, vital signs, 12-lead ECG, physical examinations, haematology and blood chemistry profiles, and urea reduction ratio.

Study G was a multicenter, multiple-dose open-label, uncontrolled gastrointestinal disorder-associated anemia study. Subjects were males and females between 18 and 60 years of age, inclusive, with moderate stable iron-deficiency anemia secondary to a gastrointestinal disorder and a calculated total iron requirement $\geqq$1000 mg; $\geqq$50% of patients in each cohort were to require $\geqq$1500 mg total iron. Duration of treatment was single doses at weekly intervals for up to 4 weeks (Cohort 1) or 2 weeks (Cohort 2). Administration of VIT-45 was by IV bolus injection of 500 mg (Cohort 1) or 1000 mg (Cohort 2), where total iron requirement for each patient, which determined how many weekly infusions were received, was calculated using the formula of Ganzoni. Examined pharmacokinetic parameters included total serum iron and pharmacodynamic (hemoglobin, ferritin, TSAT) endpoints. Examined safety parameters included adverse events, clinical laboratory evaluations, vital signs, ECG, physical examinations, and elevated serum ferritin (>500 µg/L) AND elevated TSAT (>45%).

Study H was a multicenter, multiple-dose randomized, open-label, active-controlled gastrointestinal disorder-associated anemia study. Subjects were males and females aged 18 to 80 years, inclusive, with iron-deficiency anaemia secondary to chronic inflammatory bowel disease (ulcerative colitis or Crohn's disease) and a calculated total iron requirement of at least 1000 mg total iron. Treatment was weekly VIT-45 infusions, with a maximum of 3 infusions permitted in a single treatment cycle. Administration consisted of an infusion on Day 1, with subsequent infusions at weekly intervals up to a maximum of 1000 mg iron per dose. The doses were continued until the patient received the cumulative dose based on their individual requirement for iron. Primary efficacy was examined as change from baseline to Week 12 in hemoglobin. Examined safety parameters included adverse events, vital signs, 12-lead ECG, physical examinations, and clinical laboratory evaluations.

Study I was an open label, multiple-dose, multicenter, randomized, active-control anemia due to heavy uterine bleeding study. Subjects were females at least 18 years of age with iron-deficiency anemia secondary to heavy uterine bleeding. Duration of treatment was six weeks. VIT-45 dosage was based on the calculated iron deficit as follows: where baseline TSAT$\leqq$20% or baseline ferritin$\leqq$50 ng/mL, VIT-45 total dose in mg=baseline weight (kg)×(15-baseline hemoglobin [g/dL])×2.4+500; where baseline TSAT>20% and baseline ferritin>50 ng/mL, VIT-45 total dose in mg=baseline weight (kg)×(15-baseline hemoglobin [g/dL])×2.4. For administration, $\leqq$200 mg was administered as an undiluted IVP over 1-2 minutes; 300-400 mg was administered in 100 cc NSS over 6 minutes; and 500-1,000 mg was administered in 250 cc NSS over 15 minutes. Primary efficacy was examined as the proportion of subjects achieving success, defined as an increase in hemoglobin of $\geqq$2.0 g/dL anytime between baseline and end of study or time of intervention. Examined safety parameters included adverse events, clinical laboratory evaluations, vital signs, and physical examinations.

Study J was a multicenter, single-dose blinded, randomized, placebo-controlled crossover iron deficiency anemia study. Subjects were male or female, at least 18 years of age, with a hemoglobin$\leqq$12 g/dL, TSAT$\leqq$25%, and ferritin<300 ng/mL (iron-deficiency anemia due to dialysis or non-dialysis dependent chronic kidney disease or inflammatory bowel disease), or ferritin$\leqq$100 ng/mL (iron-deficiency anemia due to other conditions). Treatment was two single doses seven days apart. Administration of VIT-45 occurred over 15 minutes and was $\leqq$1000 mg (15 mg/kg for weight $\leqq$66 kg). For pharmacokinetic variables, total serum iron was assessed using Atomic Absorption methodology. Examined safety parameters included adverse events, clinical laboratory evaluations, vital signs, and physical examinations.

TABLE 2

Summary of Safety Studies of VIT-45

| Study Number | Subjects | Intravenous Dose(s) of VIT-45 | Comparator |
|---|---|---|---|
| Pharmacokinetic Studies | | | |
| A | Total: 32<br>VIT-45: 24 | Single doses of:<br>100 mg via bolus injection<br>500 mg, 800 mg, 1000 mg diluted in 250 mL of NSS<br>administered by IV infusion over 15 minutes | Placebo |
| B | Total: 6<br>VIT-45: 6 | Single dose of 100 mg labelled with $^{52}$Fe and $^{59}$Fe<br>administered as an IV injection over 10 minutes | None |

TABLE 2-continued

Summary of Safety Studies of VIT-45

| Study Number | Subjects | Intravenous Dose(s) of VIT-45 | Comparator |
|---|---|---|---|
| | | Studies in Subjects with Postpartum Anemia | |
| C | Total: 352<br>VIT-45: 174 | Cumulative total iron requirement was calculated for each patient. Patients received IV infusions to deliver a maximum dose of 1000 mg iron per infusion. Patients received VIT-45 infusions once weekly until the calculated cumulative dose was reached or a maximum of 2500 mg had been administered. Doses ≦200 mg were administered IV push over 1–2 minutes; doses of 300–400 mg were diluted in 100 cc NSS and administered over 6 minutes; doses of 500–1000 mg were diluted in 250 cc NSS and administered over 15 minutes. | Oral iron (ferrous sulfate) 325 mg TID for 6 weeks |
| D | Total: 344<br>VIT-45: 227 | Cumulative total iron requirement was calculated for each patient using the Ganzoni formula. | Oral iron (ferrous sulfate) 100 mg BID for 12 weeks |
| | | Studies in Subjects Undergoing Hemodialysis | |
| E | Total: 237<br>VIT-45: 119 | Patients received 200 mg IV bolus injection of study drug during their scheduled hemodialysis sessions (2–3 sessions/week) until the calculated cumulative dose was reached. Cumulative total iron requirement was calculated for each patient using the Ganzoni formula. | Venofer ®; patients received 200 mg IV injection over 10 minutes of study drug during their scheduled hemodialysis sessions (2–3 sessions/week) until the calculated cumulative dose was reached. Cumulative total iron requirement was calculated for each patient using the Ganzoni formula.[a] |
| F | Total: 163<br>VIT-45: 162 | Patients received 200 mg IV push of study drug during their scheduled hemodialysis sessions (2–3 sessions/week) until the calculated cumulative dose was reached. Cumulative total iron requirement was calculated for each patient using the Ganzoni formula. | None |
| | | Studies in Subjects with Gastrointestinal Disorders | |
| G | Total: 46<br>VIT-45: 46 | 500 mg or 1000 mg iron by IV infusion at weekly intervals for up to 4 weeks (500 mg) or 2 weeks (1000 mg); maximum total dose of 2000 mg. The last dose could have been less, depending on the calculated total iron requirement. Doses were diluted in 250 cc NSS and administered by IV infusion over 15 minutes. | None |
| H | Total: 200<br>VIT-45: 137 | Cumulative total iron requirement was calculated for each patient using the Ganzoni formula. | Oral iron (ferrous sulfate) 100 mg BID for 12 weeks |
| | | Study in Subjects with Heavy Uterine Bleeding | |
| I | Total: 456<br>VIT-45: 230 | ≦1000 mg/week (15 mg/kg for weight ≦66 kg); patients received VIT-45 infusions once weekly until the calculated cumulative dose was reached or a maximum of 2500 mg had been administered. Doses ≦200 mg were administered IV push over 1–2 minutes; doses of 300–400 mg were diluted in 100 cc NSS and administered over 6 minutes; doses of 500–1000 mg were diluted in 250 cc NSS and administered over 15 minutes. | Oral iron (ferrous sulfate) 325 mg TID for 6 weeks |
| | | Study in Subjects with Iron Deficiency Anemia | |
| J | Total: 594<br>VIT-45: 584 | Single dose of ≦1000 mg by IV infusion over 15 minutes (15 mg/kg for weight ≦66 kg). Doses ≦500 mg were diluted in 100 cc NSS and doses of >500–1000 mg were diluted in 250 cc NSS. Pharmacokinetic subjects: single 1,000 mg dose by IV infusion | Placebo |

The majority of the subjects who received VIT-45 completed the study. The incidence of premature discontinuations in the completed multicenter studies was 10% in the VIT-45 group which is comparable to that observed in the oral iron (9.6%) and Venofer (13.6%) groups. Reasons for premature discontinuation were generally comparable among the treatment groups, except that the incidence of adverse events leading to discontinuation were higher in the Venofer group (5.9%) compared to the VIT-45 (1.8%) and oral iron (2.1%) groups, demonstrating the overall tolerability of VIT-45.

The overall incidences of treatment-emergent adverse events were comparable between the VIT-45 (49.5%) and oral iron (51.2%) groups in the completed multicenter studies; the incidence in the Venofer group was lower (39.0%); however, the number of subjects in the VIT-45 group is almost 10-fold that of the Venofer group. Treatment-emergent adverse events experienced by ≧2% of the 1095 VIT-45 subjects included headache (8.6%), abdominal pain (2.5%), nausea (2.4%), blood phosphate decreased (2.4%), hypertension (2.2%), nasopharyngitis (2.0%), and hypotension (2.0%). As expected, the most notable difference between subjects treated with VIT-45 and those treated with oral iron was for the incidence of gastrointestinal events (31.0% vs. 12.8%), specifically the incidences of constipation, diarrhea, nausea, and vomiting, which were more than double that observed in the VIT-45 group.

In the calculated dose/first-dose 1,000 mg studies, no statistically significant difference was observed between the VIT-45 (49.5%) and oral iron (51.2%) groups for the overall incidence of treatment-emergent adverse events. The incidence of gastrointestinal disorders was statistically significantly ($p<0.0001$) higher in the oral iron group (31.0%) compared to the VIT-45 group (15.2%), while the incidences of adverse events associated with investigations and skin and subcutaneous tissue disorders were statistically significantly higher in the VIT-45 group (9.1% and 7.3%, respectively) compared to the oral iron group (3.9% and 2.4%, respectively). Among the gastrointestinal disorders, greater proportions of subjects in the oral iron group than the VIT-45 group experienced constipation, nausea, diarrhoea, and vomiting, while a greater proportion of VIT-45 subjects experienced abdominal pain than oral iron subjects. Among the adverse events associated with investigations, greater proportions of VIT-45 subjects experienced blood phosphate decreased and GGT increased than oral iron subjects. Among the adverse events associated with skin and subcutaneous tissue disorders, greater proportions of VIT-45 subjects experienced rash and pruritus than oral iron subjects.

The only drug-related treatment-emergent adverse events reported by at least 2% of VIT-45 subjects in the calculated dose/first-dose 1,000 mg studies were headache (3.9%) and blood phosphate decreased (3.3%). The incidence of treatment-emergent adverse events reported on the first day of dosing in the calculated dose/first-dose 1,000 mg studies was statistically significant higher in the VIT-45 group compared to the oral iron group (6.8% vs. 2.7%). On the first day of dosing, the VIT-45 group had statistically significantly greater proportions of subjects who experienced general disorders and administration site conditions, primarily events associated with the site of study drug infusion, and skin and subcutaneous tissue disorders, primarily rash and urticaria, compared to the oral iron group.

The overall incidence of treatment-emergent adverse events was similar among VIT-45 subjects treated with either the 200 mg or 1000 mg doses. The only notable difference was for the higher incidence of headache in the 1000-mg group, which was almost double that observed for the 200-mg group. No meaningful trends were apparent with respect to the incidence of treatment-emergent adverse events when analyzed by gender, age, race, weight, or etiology of anemia.

There were no deaths in the study attributed to VIT-45. The incidence of other serious adverse events among VIT-45 subjects was low (3% in all completed multicenter studies and 0.3% in the placebo-controlled, single-dose crossover study) and none were considered related to study drug. The incidence of premature discontinuation due to adverse events was comparable between the VIT-45 group (2.1%) and the other active treatment groups (3.1% oral iron and 2.5% Venofer). The incidence of drug-related treatment-emergent adverse events of hypersensitivity was 0.2%, the same as that observed with oral iron (0.2%). Drug-related mild or moderate hypotension was observed in 4 (0.2%) VIT-45 subjects, none of which were considered serious, led to premature discontinuation, or were symptomatic. Treatment-emergent adverse events indicative of potential allergic reactions including rash, pruritus, and urticaria were reported by <2% of subjects who were treated with VIT-45; none of these events was considered serious and few led to premature discontinuation.

Laboratory evaluations of mean changes from baseline and potentially clinically significant values demonstrated no clinically meaningful changes for the majority of the parameters evaluated. However, during the conduct of the latter portion of the clinical program, transient, asymptomatic decreases in blood phosphate levels were observed among subjects treated with VIT-45. The decreases were apparent approximately 7 days after the initial dose of VIT-45 and the median time to recovery was approximately 2 weeks. No subjects reported an adverse event that was related to serum phosphate and no subject discontinued from the study due to decreased serum phosphate. The only predictor of change in serum phosphate was that subjects with higher baseline serum phosphate values had larger decreases in serum phosphate. The fact that the majority of oral iron-treated subjects also had a post-baseline decrease in phosphate and the negative correlation of baseline serum phosphate with changes in serum phosphate for both the VIT-45 and oral iron treatment groups suggest that the mechanism is intrinsic to iron therapy in this severely anemic population.

Overall, no clinically meaningful changes in vitals signs evaluations were associated with VIT-45 administration.

Safety data from more than 1700 subjects demonstrate the safety and tolerability of VIT-45.

What is claimed is:

1. A method of treating a disease, disorder, or condition characterized by iron deficiency or dysfunctional iron metabolism resulting in reduced bioavailability of dietary iron, comprising administering to a subject in need thereof an iron carbohydrate complex in a single dosage unit of at least about 0.6 grams of elemental iron;

wherein the iron carbohydrate complex is selected from the group consisting of an iron carboxymaltose complex, an iron mannitol complex, an iron polymaltose complex, an iron gluconate complex, and an iron sorbitol complex; and the iron carbohydrate complex has a substantially non-immunogenic carbohydrate component and substantially no cross reactivity with anti-dextran antibodies wherein said disease, disorder or condition is not Restless Leg Syndrome.

2. The method of claim 1 wherein the disease, disorder, or condition is anemia.

3. The method of claim 2 wherein the anemia is iron deficiency anemia.

4. The method of claim 3 wherein the iron deficiency anemia is associated with chronic blood loss; acute blood loss; pregnancy; childbirth; childhood development; psychomotor and cognitive development in children; breath holding spells; heavy uterine bleeding; menstruation; chronic recurrent hemoptysis; idiopathic pulmonary siderosis; chronic internal bleeding; gastrointestinal bleeding; parasitic infections; chronic kidney disease; dialysis; surgery or acute trauma; and chronic ingestion of alcohol, chronic ingestion of salicylates, chronic ingestion of steroids; chronic ingestion of non-steroidial anti-inflammatory agents, or chronic ingestion of erythropoiesis stimulating agents.

5. The method of claim 2 wherein the anemia is anemia of chronic disease.

6. The method of claim 5 wherein the chronic disease is selected from the group consisting of rheumatoid arthritis; cancer; Hodgkins leukemia; non-Hodgkins leukemia; cancer chemotherapy; inflammatory bowel disease; ulcerative colitis thyroiditis; hepatitis; systemic lupus erythematosus; polymyalgia rheumatica; scleroderma; mixed connective tissue disease; Sojgren's syndrome; congestive heart failure/cardiomyopathy; and idiopathic geriatric anemia.

7. The method of claim 2 wherein the anemia is due to impaired iron absorption or poor nutrition.

8. The method of claim 7, wherein the anemia is associated with Crohn's Disease; gastric surgery; ingestion of drug products that inhibit iron absorption; or chronic use of calcium.

9. The method of claim 1 wherein the disease, disorder, or condition is selected from the group consisting of blood donation; hair loss; and attention deficit disorder.

10. The method of claim 1 wherein the single dosage unit of elemental iron is at least about 0.7 grams.

11. The method of claim 10 wherein the single dosage unit of elemental iron is at least about 0.8 grams.

12. The method of claim 11 wherein the single dosage unit of elemental iron is at least about 0.9 grams.

13. The method of claim 12 wherein the single dosage unit of elemental iron is at least about 1.0 grams.

14. The method of claim 13 wherein the single dosage unit of elemental iron is at least about 1.5 grams.

15. The method of claim 14 wherein the single dosage unit is at least about 2.0 grams.

16. The method of claim 15 wherein the single dosage unit of elemental iron is at least about 2.5 grams.

17. The method of claim 1 wherein the single dosage unit of elemental iron is administered in about 15 minutes or less.

18. The method of claim 17 wherein the single dosage unit of elemental iron is administered in about 10 minutes or less.

19. The method of claim 18, wherein the single dosage unit of elemental iron is administered in about 5 minutes or less.

20. The method of claim 19, wherein the single dosage unit of elemental iron is administered in about 2 minutes or less.

21. The method of claim 1 wherein the iron carbohydrate complex has a pH between about 5.0 to about 7.0; physiological osmolarity; an iron core size no greater than about 9 nm; a mean diameter particle size no greater than about 35 nm; and a blood half-life of between about 10 hours to about 20 hours.

22. The method of claim 1 wherein the iron carbohydrate complex contains about 24% to about 32% elemental iron; contains about 25% to about 50% carbohydrate; and has a molecular weight of about 90,000 daltons to about 800,000 daltons.

23. The method of claim 1 wherein the iron carbohydrate complex is an iron carboxymaltose complex.

24. The method of claim 23 wherein the iron carboxymaltose complex contains about 24% to about 32% elemental iron, about 25% to about 50% carbohydrate, and is about 100,000 daltons to about 350,000 daltons.

25. The method of claim 23 wherein the iron carboxymaltose complex is obtained from an aqueous solution of iron (III) salt and an aqueous solution of the oxidation product of one or more maltodextrins using an aqueous hypochlorite solution at a pH value within the alkaline range, wherein, when one maltodextrin is applied, its dextrose equivalent lies between about 5 and about 20, and when a mixture of several maltodextrins is applied, the dextrose equivalent lies between about 5 and about 20 and the dextrose equivalent of each individual maltodextrin contained in the mixture lies between about 2 and about 20.

26. The method of claim 23 wherein:
the iron carboxymaltose complex has a chemical formula of $[FeO_x(OH)_y(H_2O)_z]_n[\{(C_6H_{10}O_5)_m(C_6H_{12}O_7)\}_l]_k$, where n is about 103, m is about 8, I is about 11, and k is about 4;
contains about 28% elemental iron; and
has a molecular weight of about 150,000 Da.

27. The method of claim 23 wherein the iron carboxymaltose complex is polynuclear iron (III)-hydroxide 4(R)-(poly-(1→4)-O-α-glucopyranosyl)-oxy-2(R),3(S),5(R),6-tetrahydroxy-hexanoate.

28. The method of claim 1 wherein the iron carbohydrate complex is an iron polyglucose sorbitol carboxymethyl ether complex.

29. The method of claim 28 wherein the iron polyglucose sorbitol carboxymethyl ether complex is a polyglucose sorbitol carboxymethyl ether-coated non-stoichiometric magnetite complex.

30. The method of claim 1 wherein the iron carbohydrate complex comprises an iron core with a mean iron core size of no greater than about 9 nm.

31. The method of claim 30 wherein the mean iron core size is at least about 1 nm but no greater than about 9 nm.

32. The method of claim 31 wherein the mean iron core size is at least about 3 nm but no greater than about 7 nm.

33. The method of claim 32 wherein the mean iron core size is at least about 4 nm but not greater than about 5 nm.

34. The method of claim 1 wherein mean size of a particle of the iron carbohydrate complex is no greater than about 35 nm.

35. The method of claim 34 wherein the particle mean size is no greater than about 30 nm.

36. The method of claim 35 wherein the particle mean size is no greater than about 25 nm.

37. The method of claim 36 wherein the particle mean size is no greater than about 20 nm.

38. The method of claim 37 wherein the particle mean size is no greater than about 15 nm.

39. The method of claim 38 wherein the particle mean size is no greater than about 10 nm.

40. The method of claim 39 wherein the particle mean size is at least 6 nm but no greater than about 7 nm.

41. The method of claim 1 wherein the iron carbohydrate complex is administered parenterally.

42. The method of claim 41 wherein the iron carbohydrate complex is administered intravenously.

43. The method of claim 42 wherein the iron carbohydrate complex is intravenously infused.

44. The method of claim 43 wherein the single unit dose of iron carbohydrate complex is intravenously infused at a concentration of about 1000 mg elemental iron in about 200 ml to about 300 ml of diluent.

45. The method of claim 44 wherein the single unit dose of iron carbohydrate complex is intravenously infused at a concentration of about 1000 mg elemental iron in about 250 ml of diluent.

46. The method of claim 44 wherein the single unit dose of iron carbohydrate complex is intravenously infused at a concentration of about 1000 mg elemental iron in about 215 ml of diluent.

47. The method of claim 42 wherein the iron carbohydrate complex is intravenously injected as a bolus.

48. The method of claim 47 wherein the single unit dose of iron carbohydrate complex is intravenously injected as a bolus at a concentration of about 1000 mg elemental iron in about 200 ml to about 300 ml of diluent.

49. The method of claim 48 wherein the single unit dose of iron carbohydrate complex is intravenously injected as a bolus at a concentration of about 1000 mg elemental iron in about 250 ml of diluent.

50. The method of claim 48 wherein the single unit dose of iron carbohydrate complex is intravenously injected as a bolus at a concentration of about 1000 mg elemental iron in about 215 ml of diluent.

51. The method of claim 41 wherein the iron carbohydrate complex is administered intramuscularly.

52. The method of claim 51 wherein the iron carbohydrate complex is intramuscularly injected at a concentration of about 500 mg elemental iron in less than about 10 ml diluent.

53. The method of claim 1 further comprising a second administration of said iron carbohydrate complex upon recurrence of at least one symptom of the disease, disorder, or condition.

54. The method of claim 1 further comprising a second administration of said iron carbohydrate complex after 1 day to 12 months after the first administration.

55. A method of treating a disease, disorder, or condition characterized by iron deficiency or dysfunctional iron metabolism resulting in reduced bioavailability of dietary iron, comprising:
intravenously administering to a subject in need thereof an iron carboxymaltose complex in a single dosage unit of at least about 1000 mg of elemental iron in about 200 ml to about 300 ml of diluent in about 5 minutes or less;
wherein the iron carboxymaltose complex comprises an iron core with a mean iron core size of at least about 1 nm but no greater than about 9 nm;
wherein mean size of a particle of the iron carboxymaltose complex is no greater than about 35 nm;
wherein the iron carboxymaltose complex is administered intravenously infused or intravenously injected at a concentration of about 1000 mg elemental iron in about 200 ml to about 300 ml of diluent.

56. The method of claim 55 wherein the iron carboxymaltose complex is obtained from an aqueous solution of iron (III) salt and an aqueous solution of the oxidation product of one or more maltodextrins using an aqueous hypochlorite solution at a pH value within the alkaline range, wherein, when one maltodextrin is applied, its dextrose equivalent lies between about 5 and about 20, and when a mixture of several maltodextrins is applied, the dextrose equivalent lies between about 5 and about 20 and the dextrose equivalent of each individual maltodextrin contained in the mixture lies between about 2 and about 20.

57. The method of claim 55 wherein the iron carboxymaltose complex is polynuclear iron (III)-hydroxide 4(R)-(poly-(1→4)-O-α-glucopyranosyl)-oxy-2(R),3(S),5(R),6-tetrahydroxy-hexanoate.

* * * * *